United States Patent
Youssef et al.

(10) Patent No.: US 9,668,795 B1
(45) Date of Patent: Jun. 6, 2017

(54) BONE PLATE SYSTEM CONFIGURABLE AS STATIC OR DYNAMIC IMPLANT

(71) Applicants: Jim A. Youssef, Durango, CO (US); Lance Hamlin, Durango, CO (US); Brian Hewko, Bay Village, OH (US)

(72) Inventors: Jim A. Youssef, Durango, CO (US); Lance Hamlin, Durango, CO (US); Brian Hewko, Bay Village, OH (US)

( * ) Notice: Subject to any disclaimer, the term of this patent is extended or adjusted under 35 U.S.C. 154(b) by 407 days.

(21) Appl. No.: 14/018,043

(22) Filed: Sep. 4, 2013

Related U.S. Application Data (62) Division of application No. 12/148,897, filed on Apr. 22, 2008, now Pat. No. 8,551,144.

(51) Int. Cl.
*A61B 17/80* (2006.01)

(52) U.S. Cl.
CPC .................... *A61B 17/809* (2013.01)

(58) Field of Classification Search
CPC . A61B 17/7059; A61B 17/80; A61B 17/8004; A61B 17/8009; A61B 17/8014; A61B 17/8019; A61B 17/8023; A61B 2017/681; A61B 17/8042; A61B 17/8047
USPC ............... 606/280–299, 105, 57, 58
See application file for complete search history.

(56) References Cited

U.S. PATENT DOCUMENTS

| | | | |
|---|---|---|---|
| 3,547,114 A | 12/1970 | Haboush | |
| 3,659,595 A * | 5/1972 | Haboush | 606/71 |
| 4,762,122 A | 8/1988 | Slocum | |
| 4,946,379 A | 8/1990 | Berchem | |
| 4,957,495 A | 9/1990 | Kluger | |
| 5,603,713 A | 2/1997 | Aust et al. | |
| 5,616,144 A | 4/1997 | Yapp et al. | |
| 5,718,705 A | 2/1998 | Sammarco | |
| 5,735,853 A * | 4/1998 | Olerud | 606/71 |
| 5,951,557 A | 9/1999 | Luter | |
| 6,117,173 A * | 9/2000 | Taddia et al. | 623/16.11 |
| 6,123,709 A | 9/2000 | Jones | |
| 6,129,730 A | 10/2000 | Bono et al. | |
| 6,258,089 B1 | 7/2001 | Campbell et al. | |
| 6,348,052 B1 | 2/2002 | Sammarco | |
| 6,533,786 B1 | 3/2003 | Needham et al. | |
| 6,562,042 B2 | 5/2003 | Nelson | |
| 6,902,565 B2 | 6/2005 | Berger et al. | |
| 6,932,820 B2 | 8/2005 | Osman | |
| 7,001,389 B1 | 2/2006 | Navarro et al. | |
| 7,044,952 B2 | 5/2006 | Michelson | |
| 7,048,739 B2 | 5/2006 | Konieczynski et al. | |
| 7,097,645 B2 | 8/2006 | Michelson | |
| 7,118,573 B2 | 10/2006 | Michelson | |

(Continued)

*Primary Examiner* — Si Ming Ku
(74) *Attorney, Agent, or Firm* — Alan W. Cannon (57) ABSTRACT

Bone plate systems and methods for implanting. A bone plate system includes a bone plate having a first surface, a second, bone contacting surface opposed to the first surface, and at least one aperture extending through the first and second surfaces. The system includes a bone screw having a threaded shank along a distal end portion thereof, the threaded shank configured to pass through the aperture. A dynamic member is configured to fit between portions of the screw and the bone plate and allow movement of the dynamic member and the screw relative to the bone plate in a first direction, while preventing movement of the dynamic member relative to the bone plate in a direction opposite to the first direction.

19 Claims, 9 Drawing Sheets

(56) References Cited

U.S. PATENT DOCUMENTS

| | | |
|---|---|---|
| 7,175,624 B2 * | 2/2007 | Konieczynski et al. ........ 606/71 |
| 7,214,226 B2 | 5/2007 | Alleyne |
| 7,278,997 B1 | 10/2007 | Mueller et al. |
| D603,964 S | 11/2009 | Kriska et al. |
| 7,651,517 B2 | 1/2010 | Konieczynski et al. |
| 8,551,144 B2 * | 10/2013 | Youssef et al. ............... 606/282 |
| 2002/0120273 A1 | 8/2002 | Needham et al. |
| 2004/0220571 A1 | 11/2004 | Assaker et al. |
| 2005/0182404 A1 | 8/2005 | Lauryssen et al. |
| 2005/0187548 A1 | 8/2005 | Butler et al. |
| 2005/0240185 A1 | 10/2005 | Boomer et al. |
| 2006/0069389 A1 | 3/2006 | Knopfle |
| 2006/0122604 A1 | 6/2006 | Gorhan et al. |
| 2006/0161157 A1 * | 7/2006 | Mosca et al. ................... 606/69 |
| 2006/0161158 A1 | 7/2006 | Orbay et al. |
| 2006/0195089 A1 | 8/2006 | LeHuec et al. |
| 2006/0217721 A1 | 9/2006 | Suh et al. |
| 2007/0016205 A1 | 1/2007 | Beutter et al. |
| 2007/0123886 A1 | 5/2007 | Meyer et al. |
| 2007/0162011 A1 | 7/2007 | Leyden et al. |
| 2007/0162013 A1 | 7/2007 | Jacene et al. |
| 2007/0203492 A1 | 8/2007 | Needham et al. |
| 2007/0225718 A1 | 9/2007 | Ensign |
| 2007/0233097 A1 | 10/2007 | Anderson et al. |
| 2007/0233112 A1 | 10/2007 | Orbay et al. |
| 2007/0276371 A1 | 11/2007 | Baynham et al. |
| 2008/0021476 A1 | 1/2008 | Kirschman |
| 2008/0097445 A1 | 4/2008 | Weinstein |
| 2008/0108998 A1 | 5/2008 | Lindemann |
| 2008/0147125 A1 | 6/2008 | Colleran et al. |
| 2008/0234681 A1 | 9/2008 | Baynham |
| 2008/0243192 A1 | 10/2008 | Jacene et al. |

\* cited by examiner

BONE PLATE SYSTEM CONFIGURABLE AS STATIC OR DYNAMIC IMPLANT

This application is a divisional application of co-pending application Ser. No. 12/148,897, filed Sep. 4, 2013, which is incorporated herein by reference in its entirety and to which application we claim priority under 35 USC §120.

FIELD OF THE INVENTION

The present invention relates to fixation devices used in orthopedic surgery, neurosurgery, and more particularly to systems, devices and methods for spinal surgery.

BACKGROUND OF THE INVENTION

Treatment of spinal injuries or disorders may include the use of a bone fixation device, such as a relatively rigid fixation rod and/or fixation plate coupled to spinal features on opposite sides of a site of injury or disorder to facilitate healing or correction of the injury or disorder. For example, it is known to attach a bone fixation plate to adjacent vertebrae to provide increased rigidity between the adjacent vertebrae in the case of a discectomy or a degenerative condition, in order to relieve pain and/or facilitate healing and/or fusion between the adjacent vertebrae.

A bone fixation plate is typically fixed across a fracture, damaged or removed disc, or other location of injury or disorder, by screwing opposite ends of the plate to healthy tissues, typically bone, on opposite sides of the location of injury or disorder, thereby rigidifying the features to which the plate is mounted to, as well as the location therebetween. In addition to providing the ability to fix the features joined by such a bone plate, it would be desirable to provide some additional, structural support, while retaining the ability of some limited relative motion between the joined features. This is particularly the case in some spinal surgeries, where it is necessary to provide some support to the columnar strength of the spinal column, but where it would also be desirable to allow some limited range of motion between vertebrae joined by a plate. The option to convert such a plate from one that completely rigidifies the vertebrae attached, relative to one another, to one that provides some rigidity and limits motion between those vertebrae, but allows a limited range of motion, and vice versa, would also be desirable.

It would further be desirable to provide a device useful not only for providing a first time solution for spinal repair, but which is additionally useful for revision surgery, or one that can span several (at least up to four) levels of the spine.

It is also common, especially in vertebral surgeries of the type described above to experience subsidence of the vertebrae after fixation of the plate thereto, such as during healing (e.g., which fusion is developing). Bone plate systems that do not allow any movement after fixation can experience failures such as partial or total pull out of one or more screws, shearing of one or more screws, or other failures induced by the compressive forces on the bone plate system caused by the subsidence. Accordingly, it would be beneficial to provide solutions that allow subsidence to occur without significantly increasing or distorting stresses imposed on the bone plate system thereby.

On the other hand, it would further be desirable to prevent or reduce the ability of bone portions fixed by a bone plate to extend away from one another, as this can delay or prevent the desired healing, and can also be painful.

Another problem with bone plate systems in general is that screws used to fix the plate to features of the patient can loosen over time, after implantation, and actually "back out" to a lesser or greater degree from their implanted positions, by reverse rotation along their thread paths. It would further be desirable to provide devices having one or more of the desirable features described above, which additionally are provided with a backout prevention mechanism to prevent such backout.

SUMMARY OF THE INVENTION

The present invention provides a bone plate system including a bone plate having a first surface, a second, bone contacting surface opposed to the first surface, and at least one aperture extending through the first and second surfaces; a bone screw having a threaded shank along a distal end portion thereof, the threaded shank configured to pass through the aperture; and a dynamic member configured to fit between portions of the screw and the bone plate and allow movement of the dynamic member and the screw relative to the bone plate in a first direction, while preventing movement of the dynamic member relative to the bone plate in a direction opposite to the first direction.

In at least one embodiment, the screw, dynamic member and aperture are configured to allow polyaxial movements of the screw relative to the bone plate.

In at least one embodiment, the dynamic member has a concave, at least partially spherical surface that mates with a convex surface of a head of the screw, the convex surface being at least partially spherical, wherein the mating surfaces allow the polyaxial movements.

In at least one embodiment, a backout prevention mechanism is provided and is configured to prevent the screw from backing out of the aperture once a proximal end of the screw head has been inserted.

In at least one embodiment, the backout prevention mechanism comprises a pair of struts extending across the aperture in a path required to be taken for backout of the screw.

In at least one embodiment, the struts also prevent backout of the dynamic member.

In at least one embodiment, the aperture extends into an undercut in the bone plate, and wherein when the screw and the dynamic mechanism move relative to the bone plate, at least a portion of the dynamic mechanism is received in the undercut, wherein a portion of the bone plate overlying the undercut prevents backout of the dynamic member.

In at least one embodiment, at least a portion of the screw is also received in the undercut, wherein a portion of the bone plate overlying the undercut prevents backout of the screw.

In at least one embodiment, the backout prevention mechanism comprises a washer.

In at least one embodiment, the washer fits in an annular groove in the aperture.

In at least one embodiment, the washer comprises a split ring washer.

In at least one embodiment, the dynamic member has a concave, at least partially spherical surface that mates with a convex surface of a head of the screw, and wherein an opening to the concave surface has an inside diameter, the head of the screw has an outside diameter at a proximal end thereof, and the backout prevention mechanism comprises the outside diameter being slightly larger than the inside diameter.

In at least one embodiment, the bone plate has a length dimension and a width dimension, the system comprising at least two sets of apertures wherein the sets are spaced lengthwise along the bone plate, each the set comprising at least one aperture.

In at least one embodiment, at least one of the apertures are each provided with a static member that is not moveable relative to the bone plate.

In at least one embodiment, the screw through the at least one aperture provided with a static member and the static member are configured to allow polyaxial movements of the screw relative to the bone plate.

In at least one embodiment, the aperture provided with a static member has a circular opening and the aperture provided with a dynamic member has an oblong opening.

In at least one embodiment, the dynamic member comprises first teeth configured to interfit with second teeth in the aperture.

In at least one embodiment, the first teeth are angled toward one of the first direction and the direction opposite to the first direction, and the second teeth are angled toward a direction opposite the direction toward which the first teeth are angled.

A bone fastener is provided, including a bone screw having a threaded shank along a distal end portion thereof, the threaded shank configured to pass through an aperture of a bone plate; and a dynamic member configured to receive a head of the screw and comprising a mechanism configured to allow movement of the dynamic member relative to the bone plate in a first direction, but to prevent movement of the dynamic member relative to the bone plate in a direction opposite to the first direction.

In at least one embodiment, the screw and the dynamic member are configured to allow polyaxial movements of the screw relative to the dynamic member.

In at least one embodiment, the dynamic member has a concave, at least partially spherical surface that mates with a convex surface of the head of the screw, the convex surface being at least partially spherical, wherein the mating surfaces allow the polyaxial movements.

In at least one embodiment, a backout prevention mechanism configured to prevent the screw from backing out of the dynamic member once a proximal end of the screw head has been inserted into the aperture distally past the backout prevention mechanism.

In at least one embodiment, the proximal end of the opening of the dynamic member has an inside diameter, the head of the screw has an outside diameter at a proximal end thereof, and the backout prevention mechanism comprises the outside diameter being slightly larger than the inside diameter.

In at least one embodiment, the dynamic member comprises teeth on an external portion thereof.

In at least one embodiment, the teeth of the dynamic member are configured to interfit with teeth in an aperture of the bone plate.

In at least one embodiment, the teeth are angled toward a first direction to prevent movement of the dynamic member in the first direction, relative to the bone plate, but to allow movement of the dynamic member is a direction opposite to the first direction, relative to the bone plate.

A method of fixing bone members is provided, the method including: fixing a first portion of a bone plate at a first bone location; fixing a second portion of the bone plate at a second bone location; allowing subsidence causing a distance between the first and second bone locations to decrease; and preventing extension of the distance between the first and second bone locations that would cause the distance to increase.

A method of fixing bone members is provided, the method including: fixing a first portion of a bone plate to a first bone location using at least one screw and at least one dynamic or static member; fixing a second portion of the bone plate to a second bone location using at least one screw and at least one dynamic or static member; wherein at least one the screw is used with the dynamic member, the dynamic member allowing movement of the dynamic member relative to the bone plate in a first direction, and preventing movement of the dynamic member relative to the bone plate in a direction opposite to the first direction.

In at least one embodiment, the first bone location is on a vertebra and the second bone location is on an adjacent vertebra.

In at least one embodiment, the vertebrae are cervical vertebrae.

In at least one embodiment, the vertebrae are thoracic vertebrae.

In at least one embodiment, the vertebrae are lumbar vertebrae.

In at least one embodiment, the method includes fixing a third portion along a length of the bone plate to a third bone location using at least one screw and at least one dynamic or static member.

In at least one embodiment, the method includes fixing a fourth portion along a length of the bone plate to a fourth bone location using at least one screw and at least one dynamic or static member.

In at least one embodiment, the method includes fixing a fifth portion along a length of the bone plate to a fifth bone location using at least one screw and at least one dynamic or static member.

In at least one embodiment, the method includes fixing a sixth portion along a length of the bone plate to a sixth bone location using at least one screw and at least one dynamic or static member.

These and other features of the invention will become apparent to those persons skilled in the art upon reading the details of the systems, fasteners and methods as more fully described below.

DETAILED DESCRIPTION OF THE INVENTION

Before the present systems, devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a screw" includes a plurality of such screws and reference to "the vertebra" includes reference to one or more vertebrae and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
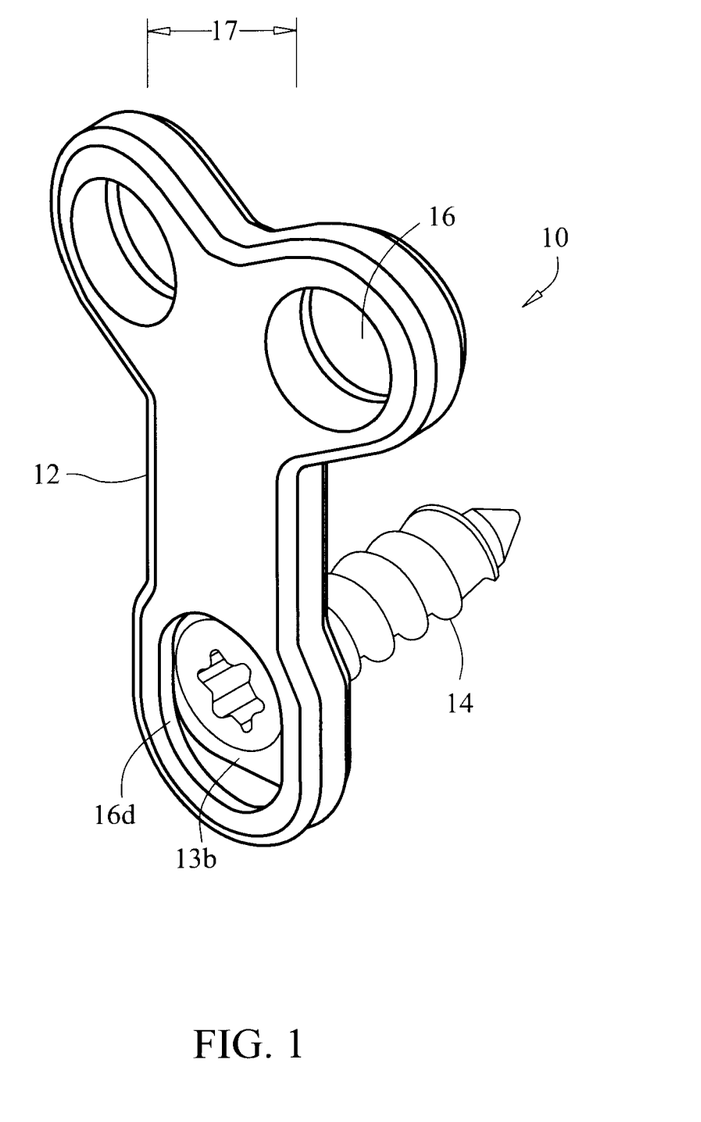
FIG. 1 illustrates one embodiment of a bone plate system according to the present invention, this embodiment being configured for a one-level vertebral application.

FIG. 1 illustrates one embodiment of a bone plate system 10 including a Y-shaped plate 1 configured to be installed across a cervical disc (which may optionally have been at least partially removed by a discectomy) and fixed anteriorly to adjacent cervical vertebrae via screws 14. Note that although FIG. 1 only shows one screw 14 for simplicity, that a complete installation of the system 10 of FIG. 1 would involve screwing three screws 14 into the vertebrae, each screw being installed through a corresponding aperture 16 in the bone plate 12.

Plate 12 is typically made of biocompatible titanium or other biocompatible metal or alloy, but may alternatively be made of a rigid biocompatible polymer or polymer composite. Plate 12 is very low profile in thickness (e.g., within a thickness range of about 2.3 mm to about 3.5 mm for use in treatment of the cervical spine) and in medial-lateral width (i.e., width 17 at the middle portion of the plate 12 for use in treatment of the cervical spine is about 9 mm to about 25 mm, in at least one embodiment, about 12 mm, and in at least one other embodiment, about 22 mm). The height of plate 12 will typically range from about 10 mm to about 100 mm for use in the cervical spine, depending upon how many levels are to be spanned, variations in dimensions among patients, etc. For thoracic spine applications, the height will typically range from about 20 mm to about 200 mm and for lumbar spine applications, the height will typically be in the range of about 30 mm to about 300 mm. Plate 12 can be implanted anteriorly on the vertebrae, or placed with either side cephalad. Other thicknesses, widths and lengths of plate 12 may be employed to use in other areas of the body, such as other bones, such as long bones, pelvis, etc. Plate 12 is not typically planar for spinal uses (although it can be, for other uses), but is biaxially domed, so that it has a curvature in the directions 27 and 29 shown in FIG. 6A (concave into the page in both dimensions). Similar curvature is provided in the single-level plate of FIG. 1 and other multi-level plates 12), so that the surface that contacts the vertebrae is concave along two axes to better conform to the anterior surfaces of the vertebrae that it is fixed to.

The embodiment of plate 12 shown in FIG. 1 has an aperture 16 pattern in one end portion thereof, that is asymmetric, relative to the aperture 16 pattern in the other end portion, so that the plate 12 (or another like it) can be inverted and installed anteriorly during revision surgery, or on either side cephalad. Advantageously, this allows the surgeon to place plate 12 in a position that provides the best fixation into the vertebral bodies anteriorly. In a revision procedure where there is retained and/or fractured hardware within the vertebral body, the necessity to place the plate 12 where it will not interfere with screws or other retained and/or fractured hardware may be necessary, and plate 12 provides flexibility in that it provides alternative placement possibilities. This allows the plate to be installed to span essentially the same location in need of treatment, while providing fresh bone into which to screw the screws 14, so that the previously formed holes and/or screws formed when placing the plate 12 9 or some other hardware) previously, do not interfere with the current implantation of a plate 12.

Figure 3:
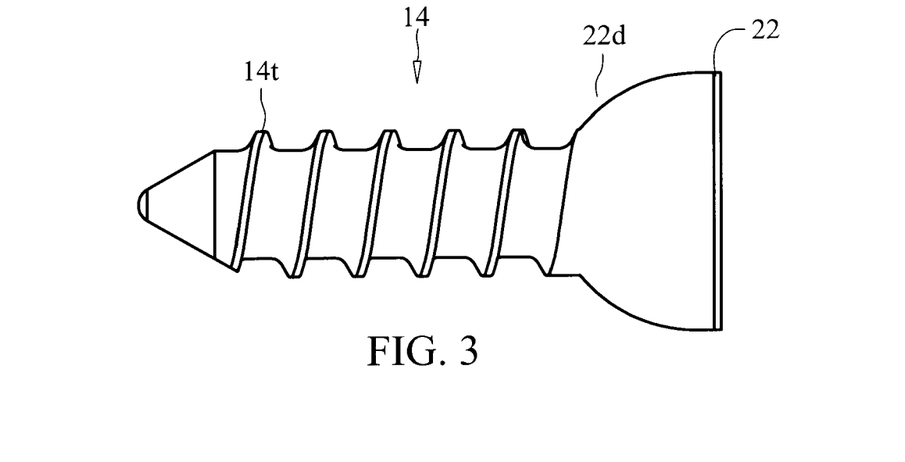
FIG. 3 is an illustration of a screw usable in embodiments of the system described herein.

The bone plate system 10 according to the present invention can be installed as a static fixation system, in which screws 14 are rigidly fixed relative to bone plate 12 and are not movable relative thereto after fixation of the system to bone. Alternatively, one or more screws 14 used may be a polyaxial screw, which, together with the aperture and or additional member provided between the aperture 16 and screw 14 upon implantation, allow screw 14 to move relative to the bone plate 12. The movement allowed can be described as a "tilting" of the screw, relative to a normal to the surface of the bone plate 12 in which the aperture 16 is formed, and this tilting can be in any direction, three hundred and sixty degrees about the aperture 16. FIG. 3 illustrates a polyaxial screw 14 and FIG. 4 schematically illustrates movement of screw 14 relative to plate 12 such that the screw 14 is oriented or "tilted" at an angle α relative to the surface of the plate 12 that the aperture 16 is formed in.

To allow these polyaxial movements, screw head 22 has a convex surface 22d (typically a spherically shaped surface) on the distal surface of the screw head that articulates with a concave surface of a race or socket 18 in the plate 12, or a concave surface of a dynamic member 30 or fixed member 50 described in more detail below. When the screw head surface 22d articulates with a surface (socket or race) 18 of the plate 12, socket 18 is provided anteriorly of and peripherally surrounding each aperture 16 through which a screw 14 can be passed during the process of fixing plate 12 to bone features. As noted, each socket 18 is provided with a concave surface or race against which convex surface 22d of the distal surface of the head 22 of screw 14 can articulate. In one embodiment, the concave surface of socket 18 is provided with a spherical curvature and the distal surface of screw head 22 is provided with a convex spherical curvature, each of the curvatures being provided so that the concave curvature has a slightly larger radius of curvature, to allow relatively free rotation between the convex surface and the concave surface.

Figure 4:
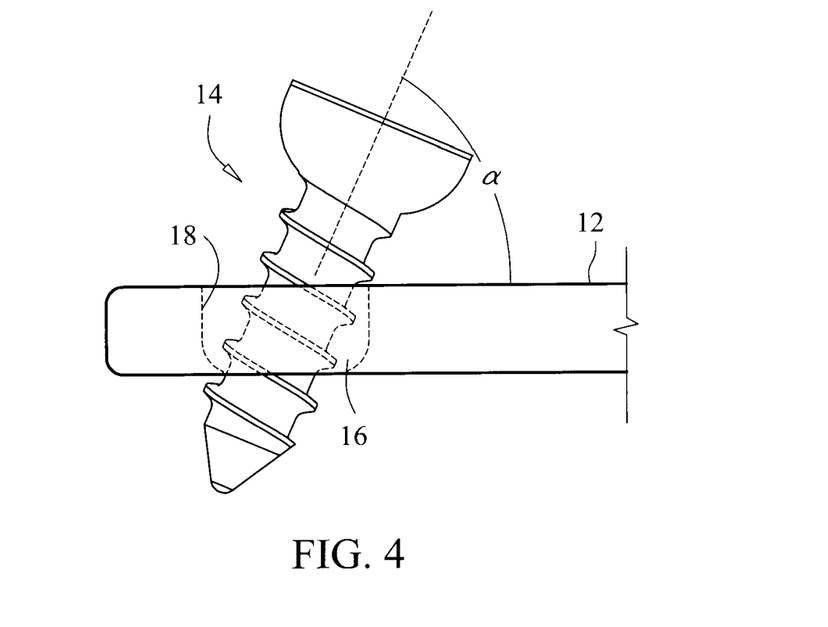
FIG. 4 illustrates one of many directional motions of a screw relative to a bone plate that is allowed by a polyaxial arrangement.

Additionally, the inside diameter of aperture 16 may be provided sufficiently larger than the largest outside diameter of the threads 14t of screw 14 (FIG. 3) to allow screw 14 to be passed through aperture 16 when screw 14 is oriented at an acute angle α relative to the anterior plane of plate 12, as illustrated in FIG. 4, thereby enabling greater versatility of available anchor sites for screws 14 when fixing plate 12 to bodily structures, as well as facilitating the ease of implantation of the screws 14, since they do not have to be perfectly normal to the anterior surface of plate 14 at the locations of the openings through which they are being inserted, in order for the screw heads 14 to be properly received by surfaces 18. In one example, the largest outside diameter of the threading of screw 14 is about 3.5 mm and the inside diameter of aperture 16 is about 3.8 mm to about 3.9 mm, allowing up to about 30 degrees of conical angulation of screw 14 from the normal to the surface of plate 12 (which equals an angle α range from 90 degrees down to about 60 degrees). Of course, the present invention is not limited to these dimensions, as they may vary to be larger or smaller, particularly depending upon the type of bone that the system is being applied to, the location of the bone and the characterization of the fracture or other abnormality being addressed, the size of the patient, etc.

To provide a better capability to allow for subsidence without substantially increasing or distorting stresses on the system, thereby greatly reducing the risk of failure of the system due to subsidence, the system 10 can be provided with one or more dynamic members 30 that, together with a cooperating configuration of plate 12 allow the dynamic member 30 and screw 14 to move relative to the plate 12. This type of movement does not require tilting of the screw 14 (although tilting is not necessarily prevented), since the dynamic member 30 is allowed to move axially along the length of plate 12, and screw 14 moves with it.

To receive the dynamic member 30, plate 12 is provided with an oblong (e.g., oval) aperture 16d. Dynamic member 30 has a width that forms a relatively close fit with aperture 16d, but has a length that is substantially less than the length of the aperture 16d. This allows dynamic member 30 to translate from one end of aperture 16d to the other. In one example, the amount of travel allowed is about 0.50 mm to about 1.00 mm, typically about 0.75 mm, but these ranges and amounts of travel may vary depending upon what bone or bones the system 10 is being anchored to, the type of malady being treated, the size and/or condition of the patient, etc.

Figure 2A:
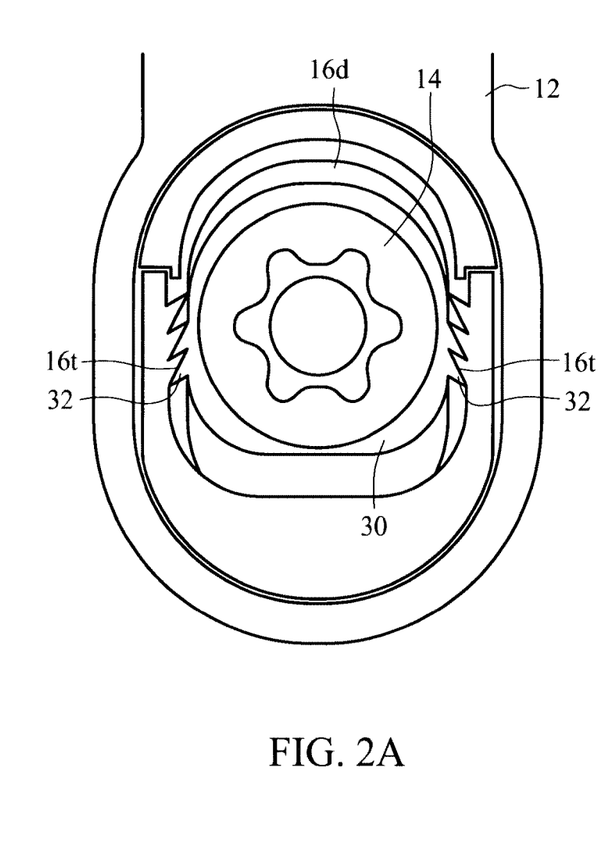
FIG. 2A is an enlarged view of an inferior end portion of the system of FIG. 1 illustrating a position of the dynamic member and screw relative to the aperture of the bone plate upon fixation of the system to bone.
Figure 2B:
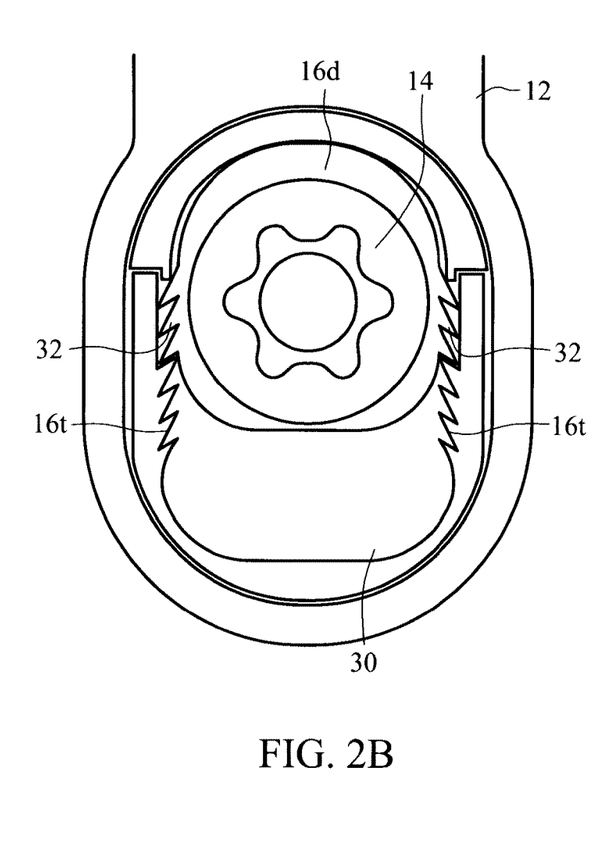
FIG. 2B is an enlarged view of an inferior end portion of the system of FIG. 1 illustrating a position of the dynamic member and screw relative to the aperture of the bone plate after subsidence has occurred.

Dynamic member 30 is further provided with teeth 32 that are configured to interfit with teeth 16t provided on bone plate 12 that extend into aperture 16d as can be best seen in FIGS. 2A-2B. Teeth 32 are angled toward the direction that they are designed to prevent the movement of dynamic member toward, relative to bone plate 12. In the example of FIGS. 1-2B, teeth 32 are angled towards the downward direction. Teeth 16t mate with teeth 32 and are angled toward the opposite direction (angled toward the upward direction in FIG. 2A). Dynamic member 30, including teeth 32 may be made from titanium, NITINOL® (nickel-titanium alloy) or other biocompatible nickel-titanium alloy or shape material, or other biocompatible metal or alloy. Accordingly, upon implantation of device 10, a fastener comprising a screw 14 having been installed in a dynamic member 30 is inserted into aperture 16t in the relative position shown in FIG. 2A, so that teeth 32 and 16t interfit as shown, and screw 14 is torqued into a target location of the bone. After complete installation of the system 10, including torquing all screws of the system 10 into the bones at the locations defined by the corresponding apertures 16,16d that the screws are inserted through, dynamic member 10 allows for subsidence of one or more bones or bone pieces relative to another that typically occurs naturally during the healing process, particularly in the cases of spinal repair.

FIG. 2B illustrates dynamic member 30 having allowed movement of bone plate 12 downward due to subsidence forces. Teeth 32 deflect inwardly somewhat when forces are applied by teeth 16t thereto in the downward direction. However, once this movement has been allowed, dynamic member 30 prevents movement of the bone plate 12 in the opposite direction relative thereto, as the engagement of the directionally angled teeth 16t,32 do not readily deflect when forces in the opposite direction are applied. Thus, for example, normal bending, extension, and other movements by a patient fitted with system 10 are not nearly sufficient to allow movement of plate 12 relative to dynamic member 30 in the opposite direct (plate upward and dynamic member downward, as shown in FIG. 2). Accordingly, dynamic member 30 advantageously allows subsidence and thus maintains the bones in contact so that they can successfully fuse, but prevents extension of the bones after the subsidence, to ensure that the proper compression and contact of bones is maintained so that the fusion/healing can process can be maintained in an uninterrupted fashion.

Dynamic members 30 may be installed in apertures 16d in one or more, up to all, of the apertures that are present in a bone plate. Thus, one or more, up to all of the screws 14 used to fix a bone plate 12 to bone may be allowed to translate along one axial direction of the plate 12, while translation in the opposite axial direction is prevented.

Alternatively, one or more screws 14 may be used to statically fix a portion of plate 12 to a bone location. Typically however, all screws used are at least configured for polyaxial motion, in a manner such as described above.

Figure 5A:
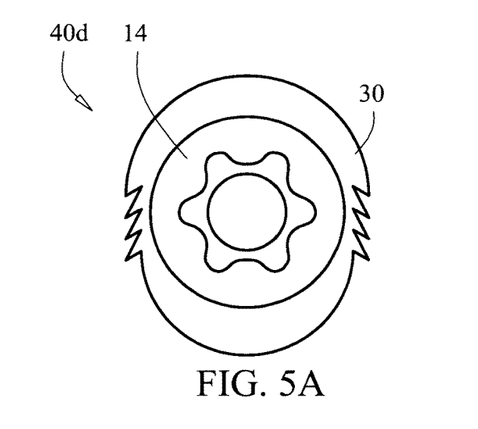
FIG. 5A illustrates a fastener according to an embodiment of the present invention.

FIG. 5A illustrates a fastener 40d for use in an aperture 16d to allow relative translation between the fastener 40d and plate 12. Thus fastener 40 includes a dynamic member 30 with a screw 14 having been installed therein. The diameter of the central opening in the dynamic member 30 may be slightly smaller than the outside diameter of the screw thread 14t so that the screw 14 needs to be threaded into the dynamic member, and is typically pre-installed to be provided as a fastener 40d for the surgical procedure. The relatively larger diameter of the screw thread helps to prevent screw backout after installation of the system 10. Additionally, the concave surface/race 34 against which the convex surface 22d of the screw head 22 articulates may be optionally cut as a spherical surface having a center of curvature 36 somewhat below the surface of the dynamic member 30 through which the opening 38 is formed. In this optional arrangement, the diameter 38d of the opening 38 at the surface is slightly smaller than the diameter 22e of the screw head 22 at the proximal end thereof. Thus, when the screw 14 is threaded into the dynamic member 30, opening 38 deflects or deforms somewhat to allow the proximal end of the screw head 22 to pass therethrough, and then recovers after the screw head passes through, as the diameter of the opening further into the opening is greater than the diameter at the surface of the opening and can readily accommodate the outside diameter of the proximal end of the screw head. The smaller diameter 38d then prevents the screw head having the larger diameter 22e from passing back out without the application of significant force.

Figure 5B:
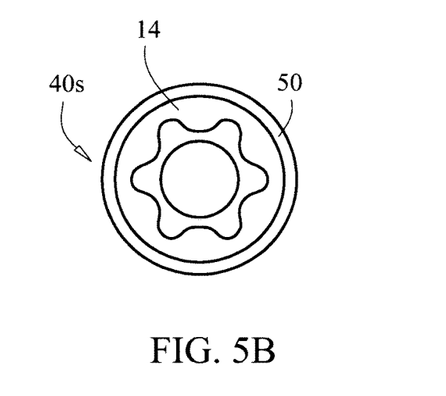
FIG. 5B illustrates a fastener with a static member.
Figure 5C:
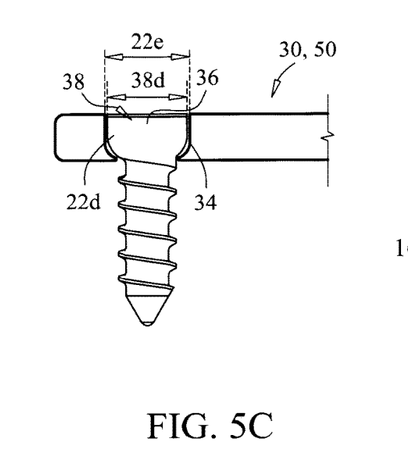
FIG. 5C illustrates a backout prevention mechanism according to an embodiment of the invention.
Figure 5D:
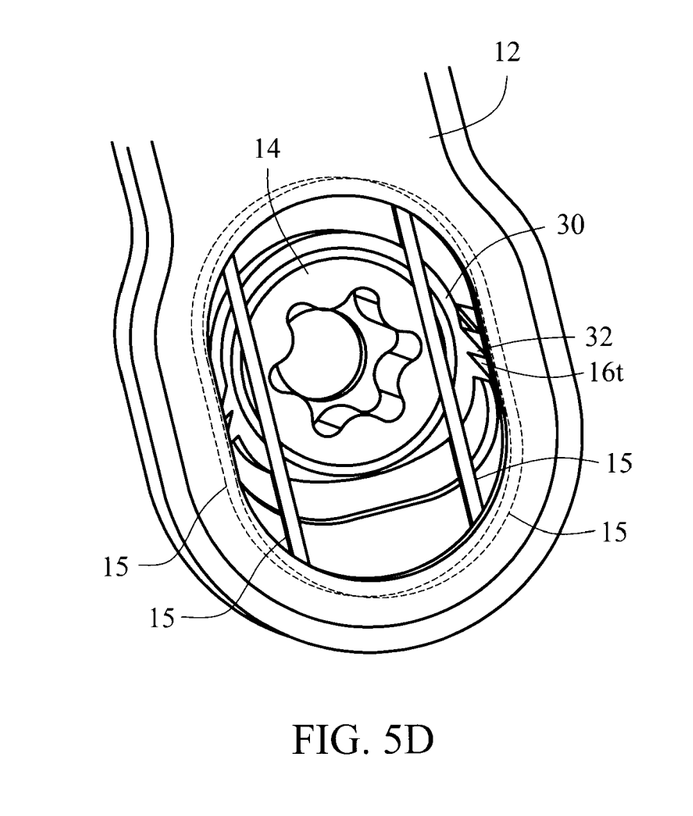
FIG. 5D illustrates another backout mechanism according to an embodiment of the present invention.

Whether or not the optional arrangement described above with regard to FIG. 5C is employed, backout prevention members 15 are provided that span oblong aperture 16d, as shown in FIG. 5D and prevent backout of dynamic member 30 as well as screw 14 by impeding the backout path of these components. It is further noted that backout prevention members 15 can also be provided to span circular aperture 16 to prevent backout of static member 50 and screw 14 in the same way as shown in FIG. 5C and described above with regard to dynamic member 30 and screw 14. Although shown as being vertically oriented with respect to plate 12, backout prevention members can be provided that span the aperture 16d, 16 in a horizontal direction, diagonal direction or other transverse orientation, which is not critical. What is important, is that the members 15 overlie the member 30, 50 and screw 14 sufficiently to impede backout, but are close enough to the perimeters of these structures so that they can deflect when a member is being inserted or removed with sufficient force to cause the deflection, and then resiliently return to their positions that impeded backout. As shown in FIG. 5D, backout prevention members 15 are resilient struts (that may be formed of spring steel, nickel-titanium alloy or other resilient metal or alloy, or resilient polymer) that bow outwardly (as indicated by phantom lines in FIG. 5D) as member 30, 50 and/or screw 14 is being inserted into place, and then resiliently return to the configuration shown in solid lines in FIG. 5D once the member 30, 50 and/or screw 14 has bypassed the struts 15. If the surgeon finds it necessary to remove screw 14, or remove member 30, 50 and screw 14, then struts 15 may again bow outwardly during the removal process, or may alternatively rupture when screw 14 is driven against members 15 with sufficient force.

Figure 5E:
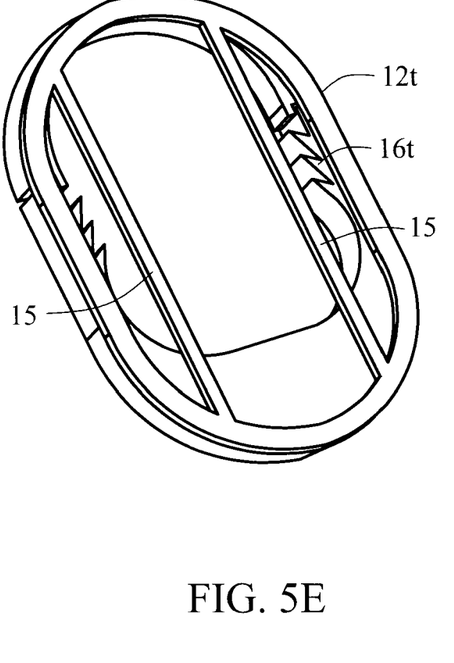
FIG. 5E illustrates a variation of the backout prevention mechanism illustrated in FIG. 5D.

Alternatively, backout prevention members 15, rather than connecting to plate 12 and thereby preventing backout of dynamic member 30 or static member 50 and screw 14, may be provided as connected to an insert 12t as illustrated in FIG. 5E. Insert 12t can be fixed in aperture 16d by press fitting, adhesive, welding or the like, whereby members 15 then function exactly as described above to prevent backout of member 30, 50 and screw 14. Although FIG. 5E shows an embodiment of insert 12t for insertion into an oblong aperture 16d for dynamic member 30 and screw 14 backout prevention, insert 12t may be made in the same manner, but circular for insertion into aperture 16 for static member 50 and screw 14 backout prevention.

Typically a backout prevention mechanism needs to be able to withstand about 3 to about 5 Newtons of force to prevent backout of a screw. The arrangement described prevents backout of screw head 22 for forces up to at least about 5 Newtons, but not greater than about 10 Newtons, so that a surgeon can unscrew the bone screw to remove it, if needed, by unscrewing to provide a backout force greater than about 10 Newtons.

Figure 5F:
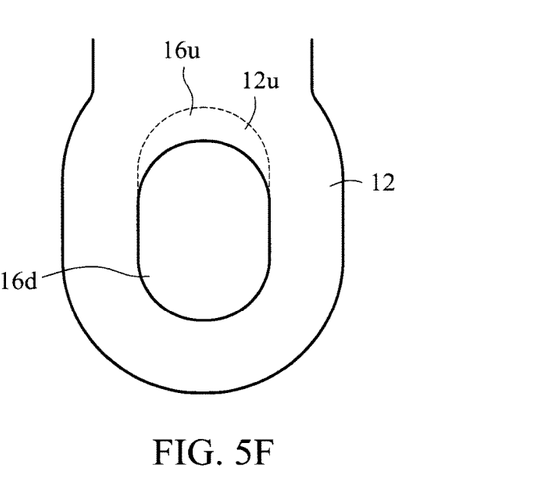
FIG. 5F illustrates a backout prevention mechanism according to an embodiment of the invention.
Figure 5G:
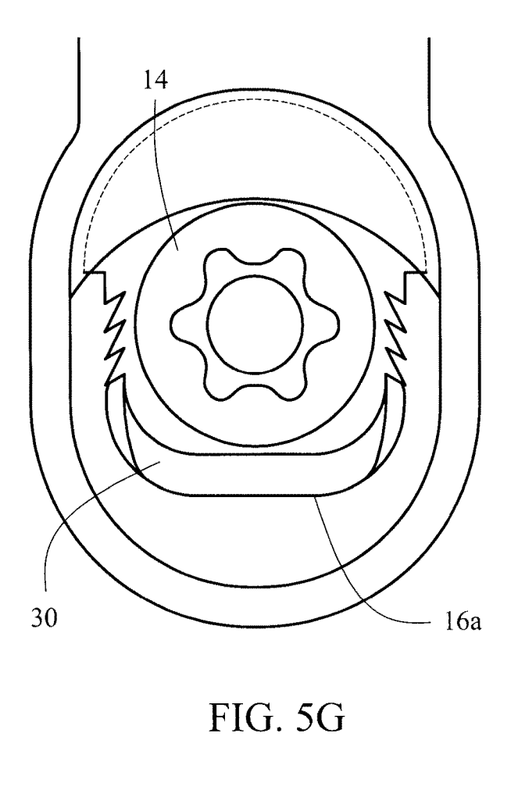
FIG. 5G illustrates backout prevention of a dynamic member by an undercut arrangement shown in FIG. 5F.
Figure 5H:
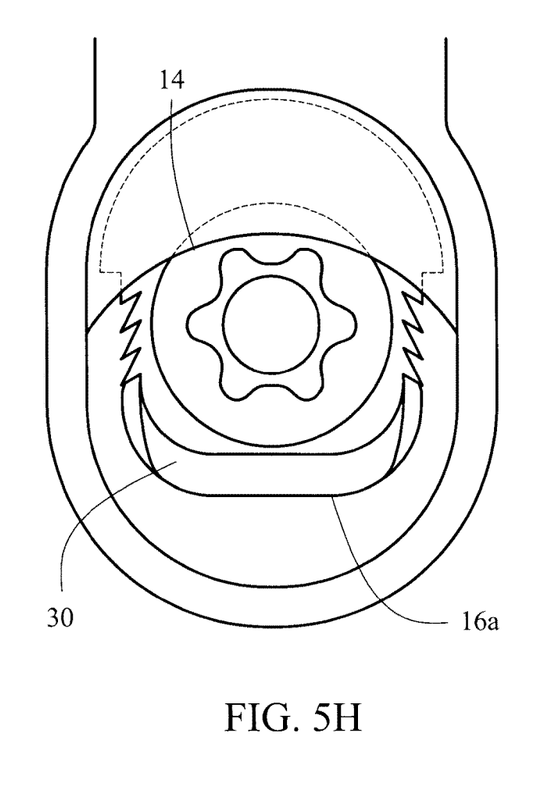
FIG. 5H illustrates backout prevention of a dynamic member and a screw by an undercut arrangement.

To aid the prevention of backout of the dynamic member, plate 12 may be optionally be provided with an undercut 16u that extends from oblong aperture 16d as illustrated in FIG. 5F, although this is typically not necessary when employing backout prevention members 15. However, by providing undercut 16u and the arrangement described above with regard to FIG. 5C, this can potentially prevent backout of screw 14 and dynamic member 30 without the use of backout prevention members 15, although this is not the preferred embodiment. As subsidence occurs and plate 12 moves relative to fastener 40d, at least a portion of fastener 40d is received in undercut 16u as illustrated in FIG. 5G, thus preventing backout of at least dynamic member 30 by the overlying portion 12u of plate 12. Optionally, undercut 12u may be dimensioned to receive an amount of fastener that also includes at least a portion of screw head 22, so that backout of screw 14 is further prevented by this mechanism (by overlying portion 12u), see FIG. 5H.

Other alternative backout prevention mechanisms that may be alternatively or additionally used, include a washer, such as a split ring washer or the like, or snap ring, that can be inserted in a groove in the opening of the member 30 or 50 proximal of the proximal surface of the screw head 22, so that the screw head butts up against this feature if backout begins, thereby preventing any further backout. A similar arrangement can be provided to prevent backout of member 30 or 50, wherein the washer, split washer or snap ring is inserted into a groove in the opening 16 or 16d.

FIG. 5B illustrates a fastener 40s for use in an aperture 16, and which does not allow relative translation between the fastener 40s and plate 12. Thus fastener 40s includes a static member 50 with a screw 14 having been installed therein. Static member typically has a circular shape and is dimensioned to fit within the circular aperture 16 so that static member 40s does not move relative to plate 12 once screw 14 has been fixed to the bone, although screw 14 may articulate relative to static member 50 and bone plate 12 when a polyaxial screw is provided as described above. The diameter of the central opening in the static member 50 may be slightly smaller than the outside diameter of the screw thread 14t so that the screw 14 needs to be threaded into the static member 50, and is typically pre-installed to be provided as a fastener 40s for the surgical procedure. The relatively larger diameter of the screw thread helps to prevent screw backout after installation of the system 10. Additionally, the concave surface/race 34 against wish the convex surface 22d of the screw head 22 articulates may be cut as a spherical surface having a center of curvature 36 somewhat below the surface of the static member 50 through which the opening 38 is formed, as illustrated in FIG. 5C, to function as a backout prevention mechanism in a manner as already described above with regard to the dynamic member 30. Backout prevention of member 50 can be provided by backout prevention members 15, as noted above, or alternative members, such as a washer, such as a split ring washer or the like, or snap ring, as noted above.

As a further alternative, screw 14 may be installed directly into the aperture 16 of the bone plate for fixation to bone. With this arrangement, the socket 18 is configured like as described above with regard to reference numeral 34, so that the socket 18 not only functions as a race for the polyaxial movements of the screw 14, but also prevents backout of the screw 14.

Systems 10 according to the present inventions are provided for at least one-, two-, three- four- and five-levels of fixation to the spinal column, where the numbers one, two, three, four and five refer to the number of disc spaces traversed by the plate 12 when anchored to the vertebrae. Systems performing greater than five levels can also be provided, using the features described herein.

Figure 6A:
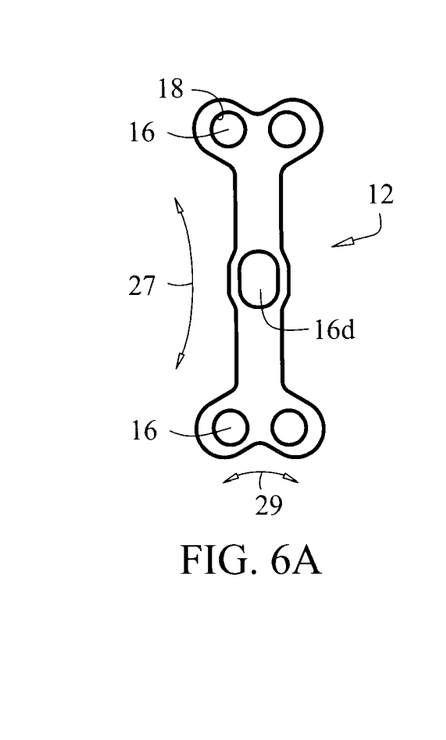
FIG. 6A illustrates an embodiment of a bone plate for use in a bone plate system configured for a two-level vertebral application, according to the present invention.
Figure 6B:
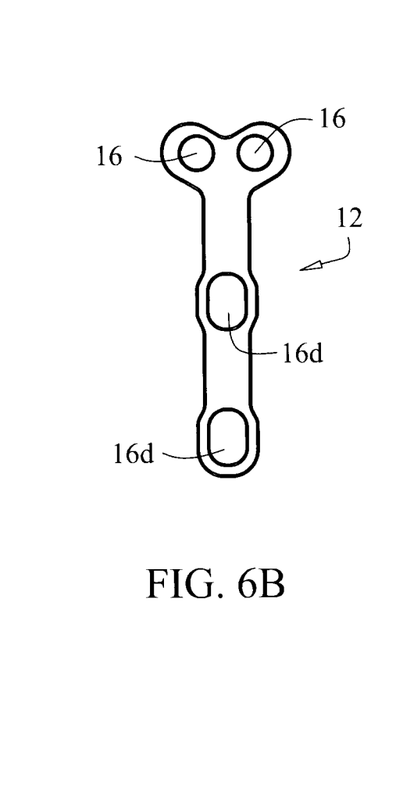
FIG. 6B illustrates an alternative embodiment of a bone plate for us in a bone plate system configured for a two-level vertebral application, according to the present invention.

FIG. 6 illustrates a two-level system 10 according to one embodiment of the present invention. In this embodiment, plate 12 includes a pair of apertures 16 at a first portion thereof, to allow fixation to a first, top-most vertebra 4 (see FIG. 11), a single oblong aperture 16d at a second portion along the length of plate 12 to allow fixation to a second, intermediate vertebra 4 and to allow dynamic, one-way movement of plate 12 relative to a fastener 40d installed therethrough, and a pair of apertures 16 at a third portion of plate 12 along the length thereof to allow fixation to a third, bottom-most vertebra 4. It is noted that this is only one non-limiting embodiment of system 10. Any set of apertures along plate 12 (where a "set" refers to one or more apertures at a particular portion of the plate, defined lengthwise) may have one or two apertures extending traverse to the lengthwise direction (or more than two, although this is typically not done, since it increases the size/width of the plate 12 unacceptably). Accordingly, any combination of sets of apertures may be provided. For example, plate 12 may have two apertures 16 at the top portion, one aperture 16d at the center portion and only one aperture 16d at the bottom portion, as illustrated in FIG. 6B (as opposed to the two apertures 16 shown in the bottom portion in FIG. 6A).

Likewise, any combination of apertures 16 and apertures 16d may be provided. Typically at least one set of apertures are provided as oblong apertures to allow dynamic movement at that portion of the plate 12. Typically a set of apertures, when the set includes more than one aperture, are all of the same type, i.e., either all apertures 16 or all apertures 16d. For all embodiments described herein, and regardless of how many levels are treated, any set of apertures may have one or two apertures, although at least one set will typically have two apertures. Also for all embodiments described herein, any set of apertures may be apertures 16 or apertures 16d.

Figure 7:
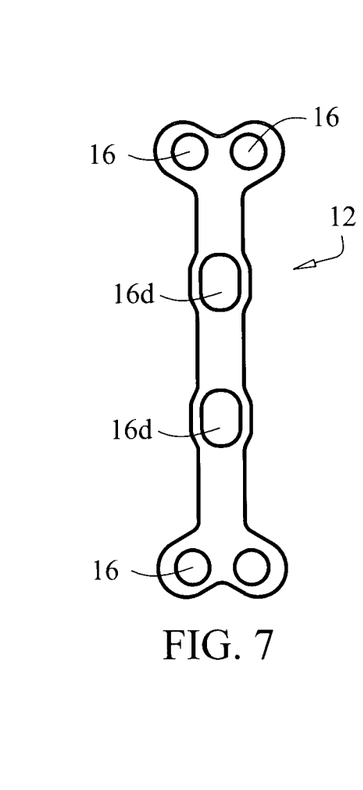
FIG. 7 illustrates an embodiment of a bone plate for use in a bone plate system configured for a three-level vertebral application, according to the present invention.

FIG. 7 illustrates an embodiment of a bone plate 12 for use in a bone plate system 10 configured for a three-level vertebral application, according to the present invention. The first set of aperture(s) in the top portion of plate 12 are configured for anchoring of screw(s) 14 into a vertebra using a static member 50 in this embodiment. The adjacent set of aperture(s) in this embodiment is a single aperture 16d configured for anchoring screw 14, via a dynamic member 30 into an adjacent vertebra. The next adjacent (third) set of aperture(s) in this embodiment is another single oblong aperture 16d for receiving a dynamic member 30 and screw 14, for anchoring screw 14 into a third adjacent vertebra. The next adjacent (fourth) set of apertures in this embodiment is a pair of apertures 16 configured for receiving static members 50 and screws 14 for anchoring screws 14 into a fourth adjacent vertebra. Note that this embodiment is also configured to receive inserts 12t, but alternatively may be configured so that backout prevention members 15 span apertures 16, 16d and connect directly to (or are integral with) plate 12.

Figure 8:
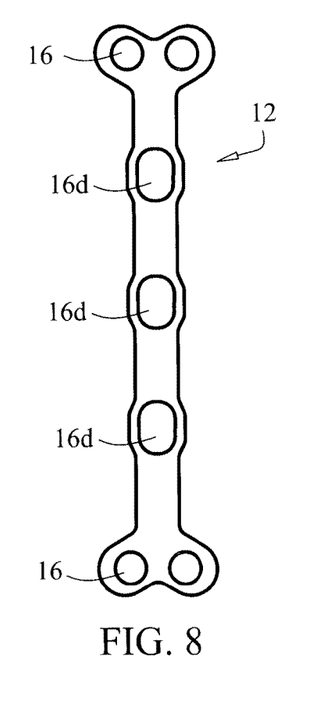
FIG. 8 illustrates an embodiment of a bone plate for use in a bone plate system configured for a four-level vertebral application, according to the present invention.

FIG. 8 illustrates an embodiment of a bone plate for use in a bone plate system configured for a four-level vertebral application, according to the present invention. The first set of aperture(s) (pair of apertures 16 in this particular embodiment) in the top portion of plate 12 are configured for anchoring of screw(s) 14 into a vertebra. The adjacent set of aperture(s) (single aperture 16d in this particular embodiment) is/are configured for anchoring screw(s) into an adjacent vertebra. The next adjacent (third) set of aperture(s) (single aperture 16d in this particular embodiment) is/are configured for anchoring screw(s) into a third adjacent vertebra. The next adjacent (fourth) set of aperture(s) (single aperture 16d in this particular embodiment) is/are configured for anchoring screw(s) into a fourth adjacent vertebra. The next adjacent (fifth) set of aperture(s) (pair of apertures 16 in this particular embodiment) are configured for anchoring screw(s) into a fifth adjacent vertebra.

Figure 9:
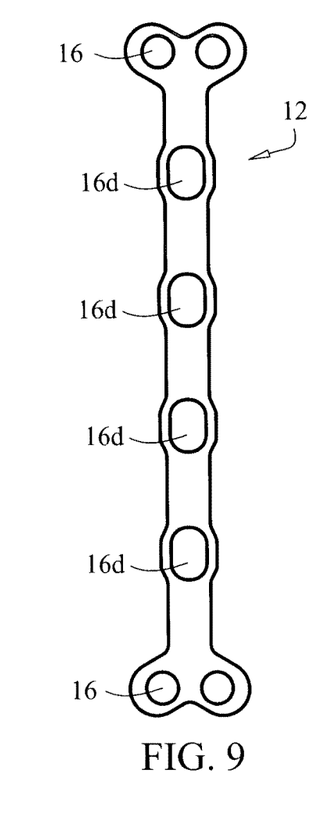
FIG. 9 illustrates an embodiment of a bone plate for use in a bone plate system configured for a five-level vertebral application, according to the present invention.

FIG. 9 illustrates an embodiment of a bone plate for use in a bone plate system configured for a five-level vertebral application, according to the present invention. The first set of aperture(s) (pair of apertures 16 in this particular embodiment) in the top portion of plate 12 is/are configured for anchoring of screw(s) 14 into a vertebra. The adjacent set of aperture(s) (single aperture 16d in this particular embodiment) is/are configured for anchoring screw(s) into an adjacent vertebra. The next adjacent (third) set of aperture(s) (single aperture 16d in this particular embodiment) is/are configured for anchoring screw(s) into a third adjacent vertebra. The next adjacent (fourth) set of aperture(s) (single aperture 16d in this particular embodiment) is/are configured for anchoring screw(s) into a fourth adjacent vertebra. The next adjacent (fifth) set of aperture(s) (single aperture 16d in this particular embodiment) is/are configured for anchoring screw(s) into a fifth adjacent vertebra. The next adjacent (sixth) set of aperture(s) (pair of apertures 16 in this particular embodiment) is/are configured for anchoring screw(s) into a sixth adjacent vertebra.

Figure 10:
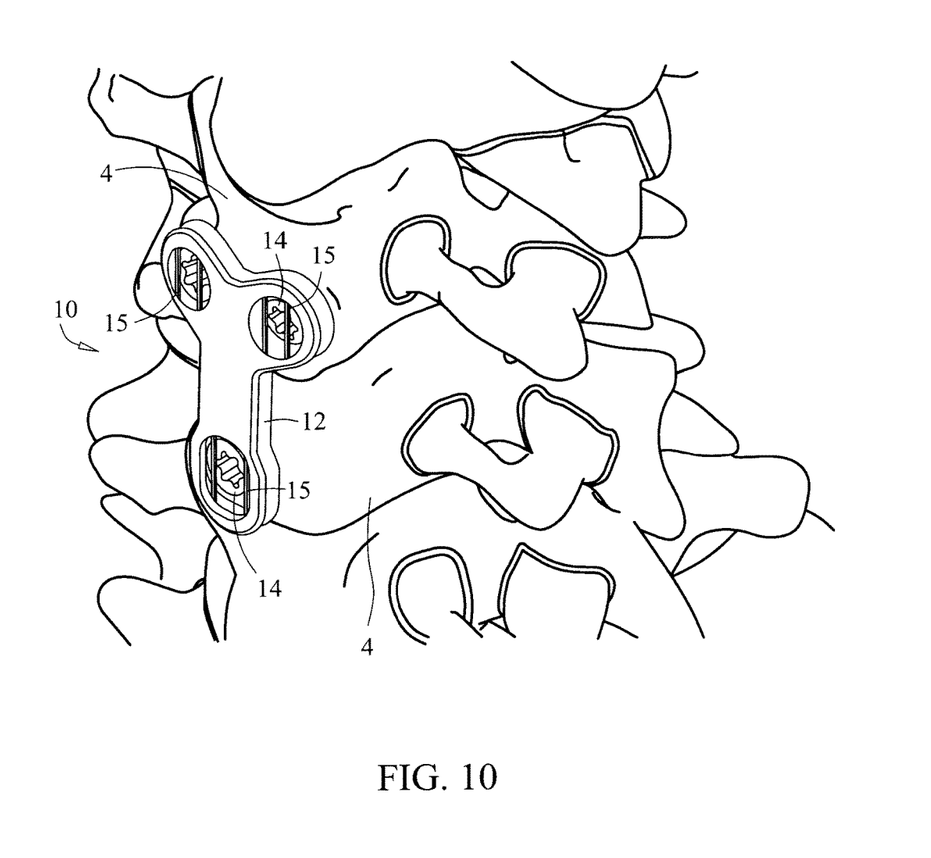
FIG. 10 illustrates an embodiment of a bone plate system employing a one-level bone plate, with screws and static members employed at the top set of apertures of the plate and with a screw and dynamic member employed at the bottom aperture of the plate.

FIG. 10 illustrates system 10 in a single level configuration having been installed anteriorly on a pair of adjacent cervical vertebrae. In this embodiment, system 10 includes plate 12 having static members 50 and screws 14 inserted through the top set of apertures 16 with screws 14 having been screwed into a first vertebra 4 and the bottom set being an oblong aperture 16d with dynamic member 50 and screw 14 inserted therethrough. Screw 14 has been screwed into the inferiorly adjacent vertebrae 4 to fix the bottom portion of plate 12 thereto while still allowing subsidence to occur. In this way, the top vertebra 4 fixed by the top portion of plate 12 and screws 14 can subside (i.e., move or gravitate toward the inferiorly adjacent vertebra 4) because dynamic member 50 allows plate 12 to move in an inferior direction relative to the inferiorly adjacent vertebra 4. After implanting the screws 14 into the respective vertebrae 4, screws 14 are prevented from backout by the backout prevention mechanisms described above. While allowing subsidence, as described above, dynamic member 50 prevents upward relative movement of plate 12 relative to the inferior adjacent vertebra 4 that the bottom portion of plate 12 is anchored to in this embodiment. Accordingly, subsidence is accommodated while extension is prevented.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A bone plate assembly comprising: a bone screw having a threaded shank along a distal end portion thereof, a bone plate having an aperture, said threaded shank configured to pass through the aperture of the bone plate;
    a dynamic member configured to receive a head of said screw and comprising a mechanism configured to allow movement of said dynamic member relative to the bone plate in a first movement direction, but to prevent movement of said dynamic member relative to the bone plate in a direction opposite to said first movement direction; and
    a backout prevention member comprising an undercut extending from the aperture into the bone plate, configured so that at least a portion of said dynamic member and a portion of said head of said screw are overlaid by said bone plate when entering into said undercut, to prevent backout of said dynamic member and said screw during use.

2. The assembly of claim 1, wherein said screw and said dynamic member are configured to allow polyaxial movements of said screw relative to said dynamic member.

3. The assembly of claim 2, wherein said dynamic member has a concave, at least partially spherical surface that mates with a convex surface of said head of said screw, said convex surface being at least partially spherical, wherein said mating surfaces allow said polyaxial movements.

4. The assembly of claim 1, further comprising a second backout prevention mechanism configured to prevent said screw from backing out of said dynamic member once a proximal end of said screw head has been inserted into said aperture distally past said second backout prevention mechanism.

5. The assembly of claim 4, wherein an opening of said dynamic member at a proximal end thereof has an inside diameter, said head of said screw has an outside diameter at a proximal end thereof, and said second backout prevention mechanism comprises said outside diameter being slightly larger than said inside diameter.

6. The assembly of claim 1, wherein said dynamic member comprises teeth on an external portion thereof.

7. The assembly of claim 6, wherein said teeth of said dynamic member are configured to interfit with teeth in the aperture of the bone plate.

8. The assembly of claim 6, wherein said teeth are angled toward a first teeth direction to prevent movement of said dynamic member in said first movement direction, relative to the bone plate, but to allow movement of said dynamic member is a direction opposite to said first movement direction, relative to the bone plate.

9. The assembly of claim 1, wherein said backout prevention member further comprises at least one strut extending over at least a portion of at least one of said dynamic member and said bone screw.

10. A method of fixing bone members, said method comprising:
    fixing a first portion of a bone plate at a first bone location;
    fixing a second portion of the bone plate at a second bone location;
    providing a backout prevention member to prevent backout of a dynamic member and a screw used in fixing at least one of said first portion and said second portion; and
    allowing subsidence causing a distance between the first bone location and the second bone location to decrease;
    and preventing extension of said distance between the first bone location and the second bone location that would cause said distance to increase; and
    during said subsidence, at least a portion of said dynamic member and at least a portion of said screw slide into an undercut in said bone plate.

11. A method of fixing bone members, said method comprising:
    fixing a first portion of a bone plate to a first bone location using at least one screw and at least one dynamic or static member;
    fixing a second portion of the bone plate to a second bone location using at least one screw and at least one dynamic or static member; and
    providing a backout prevention member to prevent backout of at least one of the dynamic member or the static member;
    wherein at least one of said screws is used with said dynamic member, said dynamic member allowing movement of said dynamic member relative to said bone plate in a first movement direction, and preventing movement of said dynamic member relative to said bone plate in a direction opposite to said first movement direction; and
    and, during movement in said first direction, at least a portion of said dynamic member and at least a portion of said screw used with said dynamic member slide into an undercut in said bone plate so that said bone plate overlies said at least a portion of said dynamic member and said at least a portion of said screw.

12. The method of claim 11, wherein said first bone location is on a vertebra and said second bone location is on an adjacent vertebra.

13. The method of claim 12, wherein said vertebrae are cervical vertebrae.

14. The method of claim 12, wherein said vertebrae are thoracic vertebrae.

15. The method of claim 12, wherein said vertebrae are lumbar vertebrae.

16. The method of claim 11, further comprising:
    fixing a third portion along a length of the bone plate to a third bone location using at least one screw and at least one dynamic or static member.

17. The method of claim 16, further comprising:
fixing a fourth portion along a length of the bone plate to a fourth bone location using at least one screw and at least one dynamic or static member.

18. The method of claim 17, further comprising:
fixing a fifth portion along a length of the bone plate to a fifth bone location using at least one screw and at least one dynamic or static member.

19. The method of claim 18, further comprising:
fixing a sixth portion along a length of the bone plate to a sixth bone location using at least one screw and at least one dynamic or static member.

* * * * *